United States Patent
Nordstrom et al.

(10) Patent No.: US 10,247,648 B2
(45) Date of Patent: Apr. 2, 2019

(54) HIGH PRECISION QUANTIFICATION OF SUB-VISIBLE PARTICLES

(71) Applicant: Intelligent Virus Imaging Inc., Southern Pines, NC (US)

(72) Inventors: Rickard Nordstrom, Tullinge (SE); Ida-Maria Sintorn, Sollentuna (SE); Lars Haag, Nykvarn (SE)

(73) Assignee: Intelligent Virus Imaging Inc., Southern Pines, NC (US)

( * ) Notice: Subject to any disclaimer, the term of this patent is extended or adjusted under 35 U.S.C. 154(b) by 0 days.

(21) Appl. No.: 15/736,621

(22) PCT Filed: Oct. 21, 2016

(86) PCT No.: PCT/US2016/058011
§ 371 (c)(1),
(2) Date: Dec. 14, 2017

(87) PCT Pub. No.: WO2017/105625
PCT Pub. Date: Jun. 22, 2017

(65) Prior Publication Data
US 2018/0172566 A1    Jun. 21, 2018

Related U.S. Application Data

(60) Provisional application No. 62/269,465, filed on Dec. 18, 2015.

(51) Int. Cl.
*G01N 1/40* (2006.01)
*G01N 15/14* (2006.01)
*G01N 15/00* (2006.01)

(52) U.S. Cl.
CPC ............ *G01N 1/4077* (2013.01); *G01N 15/14* (2013.01); *G01N 15/1468* (2013.01); *G01N 2001/4088* (2013.01); *G01N 2015/0038* (2013.01); *G01N 2015/1486* (2013.01)

(58) Field of Classification Search
CPC .. G01N 1/4077; G01N 15/14; G01N 15/1468; G01N 2015/1486; G01N 2015/0038
See application file for complete search history.

(56) References Cited

U.S. PATENT DOCUMENTS

| | | | | |
|---|---|---|---|---|
| 2002/0168757 A1* | 11/2002 | Kirk | ...................... | B01L 3/5025 435/288.5 |
| 2003/0024877 A1 | 2/2003 | Amann et al. | | |
| 2010/0151446 A1 | 6/2010 | Homman | | |
| 2011/0041591 A1* | 2/2011 | Gupta | ................... | B01L 3/5023 73/64.56 |

\* cited by examiner

*Primary Examiner* — Nicole M Ippolito
*Assistant Examiner* — Sean M Luck
(74) *Attorney, Agent, or Firm* — Fasth Law Offices; Rolf Fasth

(57) ABSTRACT

The method is for quantification of sub-visible particles. A filter membrane is provided that has a plurality of pores defined therethrough. The filter membrane is in operational engagement with a vacuum chamber. The pores are sealed with a sealant. A sample droplet, containing a liquid and sub-visible particles, is applied onto the filter membrane. The liquid dissolves the sealant in pores disposed directly below the sample droplet. The liquid flows through the pores in which the sealant has been dissolved and the sub-visible particles remain on top of the filter membrane. The particles are enumerated in an electron microscopy.

8 Claims, 6 Drawing Sheets

HIGH PRECISION QUANTIFICATION OF SUB-VISIBLE PARTICLES

PRIOR APPLICATION

This application is a U.S. national phase application based on International Application No. PCT/US2016/058011, filed 21 Oct. 2016, claiming priority from U.S. Provisional Patent Application No. 62/269,465, filed 18 Dec. 2015.

TECHNICAL FIELD

The present invention relates to a method for high precision quantification of sub-visible particles, such as microparticles and/or nanoparticles, using microscopy such as scanning electron microscopy (SEM).

BACKGROUND AND SUMMARY OF THE INVENTION

A precise enumeration of the number of sub-visible particles such as virus particles, virus-like particles, inorganic and polymeric beads and other nanoparticles and micro-particles from liquid samples is important in many processes. For example, modified virus vectors are commonly used in gene therapy applications. The number of active vectors per mL (the infectious titer of the virus sample) can be determined using standard infectivity assays. However, by using the currently available methods, it is not possible to precisely determine the total number of particles, including non-infectious particles, in the sample. The ratio of infectious over non-infectious particles provides invaluable information about the quality and efficacy of the final gene therapy product and the upstream development processes.

One major limitation of the currently available techniques, such as quantitative flow cytometry (QFCM), is that the nanoparticles of interest are not directly detected. Instead, the number of bound probes to a population of nanoparticles is quantitated. Since the number of probes that binds per nanoparticle varies, the precision of the conventional indirect techniques is typically low and dependent on the affinity between the specimen and probe. A technique where the nanoparticle of interest could be directly detected would overcome this limitation. Moreover, if the technique would be able to visualize the particles at sufficient resolution, individual particles could be identified based on their size and morphology and thus be directly enumerated. Even particles within clusters could be enumerated and estimated. This is not possible by using the currently available affinity methods or light scattering-based techniques.

The novel high-precision direct particle method of the present invention may be used to enumerate both inorganic and organic sub-visible particles, such as nanoparticles, from liquid samples. One important feature is that the specimens are applied on a well-defined and measurable footprint. Another important feature is that the specimens are more evenly distributed than what has been possible before and this reduces the need for sampling and it is now possible to conduct the analysis at a resolution where the individual particles can easily be identified. The sub-visible particles are directly detected without the need for signal probes and can be visualized in normal two-dimensional images. The particle quantification SEM (pqSEM) method of the present invention is preferably based on low-vacuum filtering, scanning electron microscopy (SEM) or other electron microscopy techniques and image analysis. The present invention can be used with or without internal standards, of which an example would be National Institute of Standards and Technology (MIST) characterized polystyrene beads.

The present invention provides a solution to the above described problems. More particularly, the method is for quantification of sub-visible particles. A filter membrane is provided that has a plurality of pores defined therethrough. The filter membrane is in operational engagement with a vacuum chamber. The pores are sealed with a sealant. A sample droplet, containing a liquid with sub-visible particles, is applied onto the filter membrane. The liquid dissolves the sealant in the pores located directly below the sample droplet. The liquid flows through the pores in which the sealant has been dissolved and the sub-visible particles remain on top of the filter membrane. The filter membrane, with the particles disposed thereon, is moved to an electron microscope and enumerated in images acquired in the microscope.

The method further comprises the step of pre-mounting a filter assembly, containing the filter membrane, onto a SEM support.

The method further comprises the step of placing a mounting tape on the SEM support.

The method further comprises the step of providing the SEM support, having an elongate channel defined therein, using an injector containing the sample droplet, and aligning the injector on top of an elongate channel prior to depositing the sample droplet on the filter membrane.

The method further comprises the step of connecting the SEM support to a vacuum chamber connected to a vacuum source and subjecting the filter membrane to a suction force via the elongate channel.

The method further comprises the step of depositing the sample droplet onto the filter membrane without the sample droplet touching any outside edge of the filter membrane.

The method further comprises the step of the liquid only dissolving the sealant in the pores disposed directly below the sample droplet while the adjacent pores on the side of the droplet remain sealed with the sealant because the liquid has not been in contact with the sealant disposed in those pores.

The method further comprises the step of the sub-visible particles forming a defined and measurable footprint on the filter membrane and acquiring a series of images of the particles from an outside periphery of the footprint to the center of the footprint.

The method further comprises the step of counting the particles in the electron microscopy images acquired at a resolution where the particles are clearly visible—either manually or automatically using image analysis methods.

The method further comprises the step of estimating the total area of the footprint on the filter membrane in microscopy images covering the whole footprint (either one low-magnification image covering the whole footprint or several higher magnification sub-images of the footprint stitched together).

The method further comprises the step of calculating the total number of particles in the sample from the area of the whole footprint and the number of particles per area unit derived from images at a resolution high enough to clearly see single particles.

The method further comprises the step of possibly compensating for uneven radial particle distribution of the particles in the footprint for which information is derived from acquiring a series of images from the periphery of the footprint through the center at a high enough magnification to clearly see individual particles.

The method further comprises the step of calculating the concentration of particles in the solution using the total particle estimate from the footprint; the applied volume and dilution of the liquid sample.

The method further comprises the step of using a diluent of the liquid to dissolve the sealant in the pores located directly below the sample droplet. The specimen should be in a liquid form and the diluent should be compatible with the diluent and have the property of effectively dissolving the sealant that is being used.

The method further comprises the step of using glycine as the sealant. Other sealants that could be used include, but are not limited to, trehalose/sucrose-based sealants.

DETAILED DESCRIPTION

Figure 1:
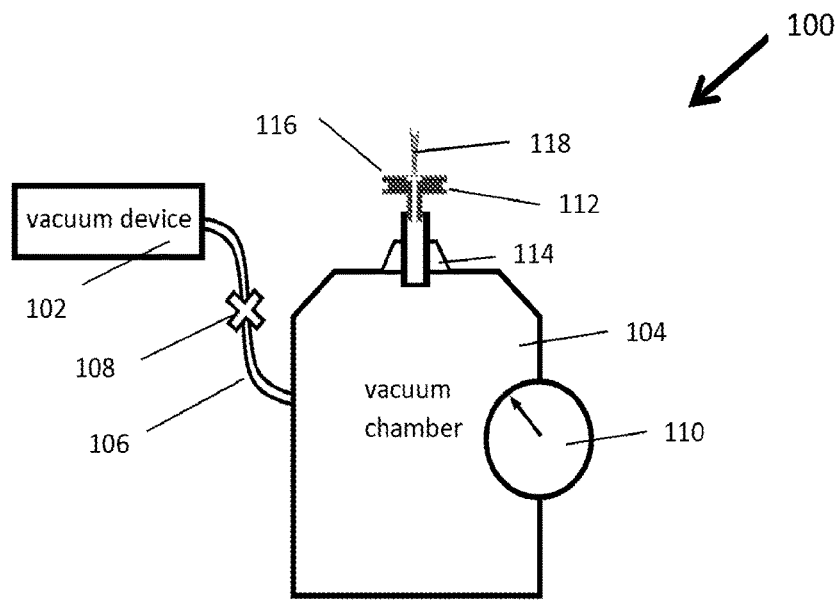
FIG. 1 is a schematic elevational side view of a vacuum device of the present invention.

The method of the present invention is described with reference to FIGS. 1-6. FIG. 1 is a schematic front view of a vacuum assembly 100 that has a vacuum device 102 connected to a vacuum chamber 104 via a tubing 106 extending therebetween. Preferably, the tubing 106 has a suitable valve such as a luer valve 108. A vacuum manometer 110 is in operative engagement with the vacuum chamber 104 to measure a vacuum pressure therein. A filter assembly 112 is mounted by a filter assembly mount 114 on top of the vacuum chamber 104. A filter membrane 116 is disposed on the filter assembly 112. An injector 118 is located above the filter membrane 116.

Figure 2:
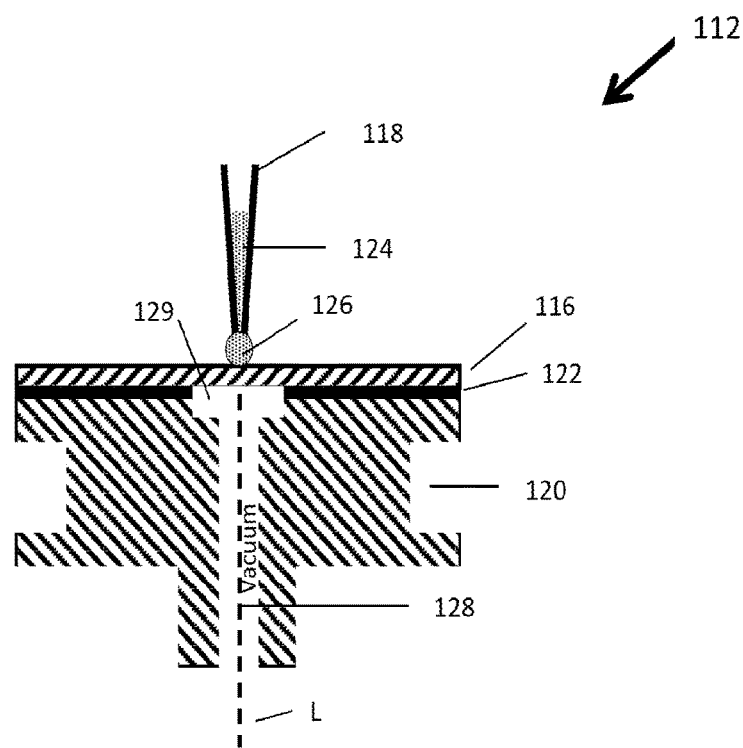
FIG. 2 is a schematic cross-sectional side view of the filter assembly.

FIG. 2 is a schematic cross-sectional view of the filter assembly 112. The entire analysis process of the present invention may be simplified by pre-mounting the filter membrane 116 onto the SEM support (alumina stub) 120 instead of doing it manually when the filter membrane 116 contains the sample/specimen to be analyzed and enumerated. The mounting may be done by simply drilling a hole in the SEM stub 120. The use of such a device minimizes the risk of losing specimen or damaging the filter membrane 116 during the previous setup in which the filter membrane 116 that contains the specimen is handled manually during the mounting onto the SEM stub 120. The details of the preparation of the filter membrane 116 are discussed below. Such a pqSEM analytical consumable device is relatively inexpensive to manufacture.

More particularly, the filter assembly 112 preferably has a modified SEM alumina stub 120 onto which a double-sided carbon mounting tape 122 is placed. The sealed porous filter membrane 116 is placed on top of the carbon mounting tape 122. The process of sealing the filter membrane 116 is described in detail below particularly with reference to FIGS. 5-6. The injector 118, that contains a specimen or sample 124 to be analyzed, is disposed or positioned above the filter membrane 116 and is used to deposit a sample droplet 126 onto the filter membrane 116. Because the stub 120 is sealingly connected to the filter assembly mount 114 that, in turn, is mounted on the vacuum chamber 104, there is vacuum inside the stub 120 so that the vacuum exerts a suction force on the filter membrane 116 from below the filter assembly 112. This is enabled because an elongated cavity or channel 128, defined inside the stub 120, is in fluid communication with the filter membrane 116 and the vacuum chamber 104. As described below, it is important that the injector 118 is correctly positioned above the filter membrane 116 so that when the sample droplet 126 is deposited onto the filter membrane 116, the sample droplet 126 is not in contact with edges of the filter membrane 116 and placed directly above an enlarged cavity portion 129 that is defined between channel 128 and the underside of the mounting tape 122. Preferably, the droplet 126 is placed at or near the center of the cavity portion 129 that is aligned with a longitudinal axis (L) that extends through the channel 128.

Figure 3A:
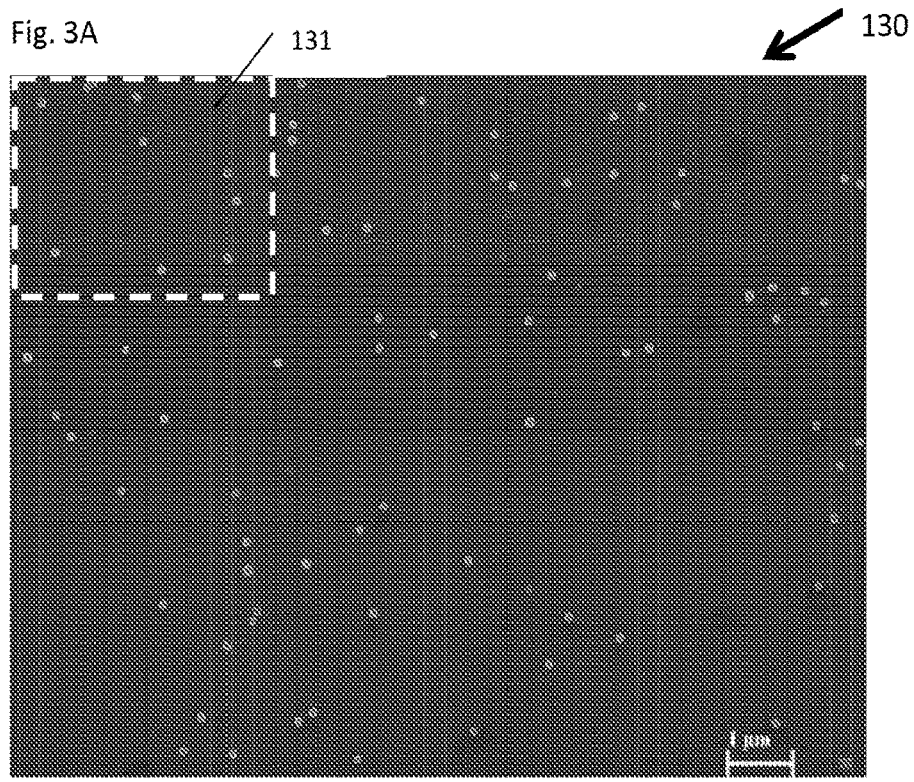
FIG. 3A is an unprocessed high magnification SEM image of polystyrene beads adhered to a poly-ether sulfone filter.
Figure 3B:
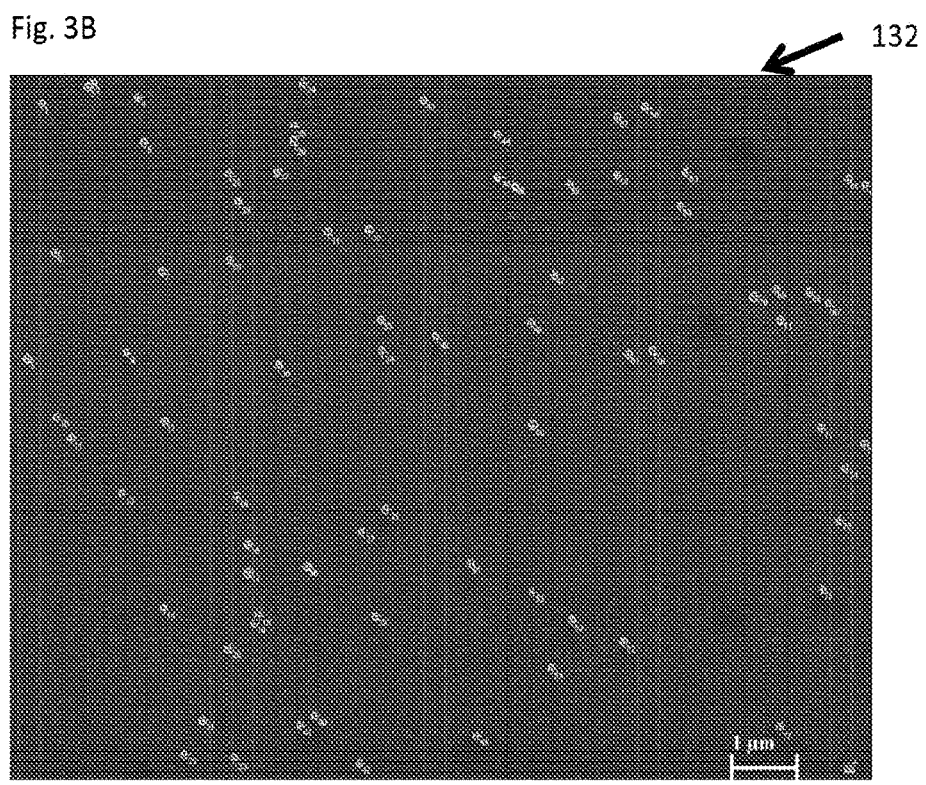
FIG. 3B is a detected and enumerated high magnification SEM image of polystyrene beads adhered to a poly-ether sulfone filter.
Figure 3C:
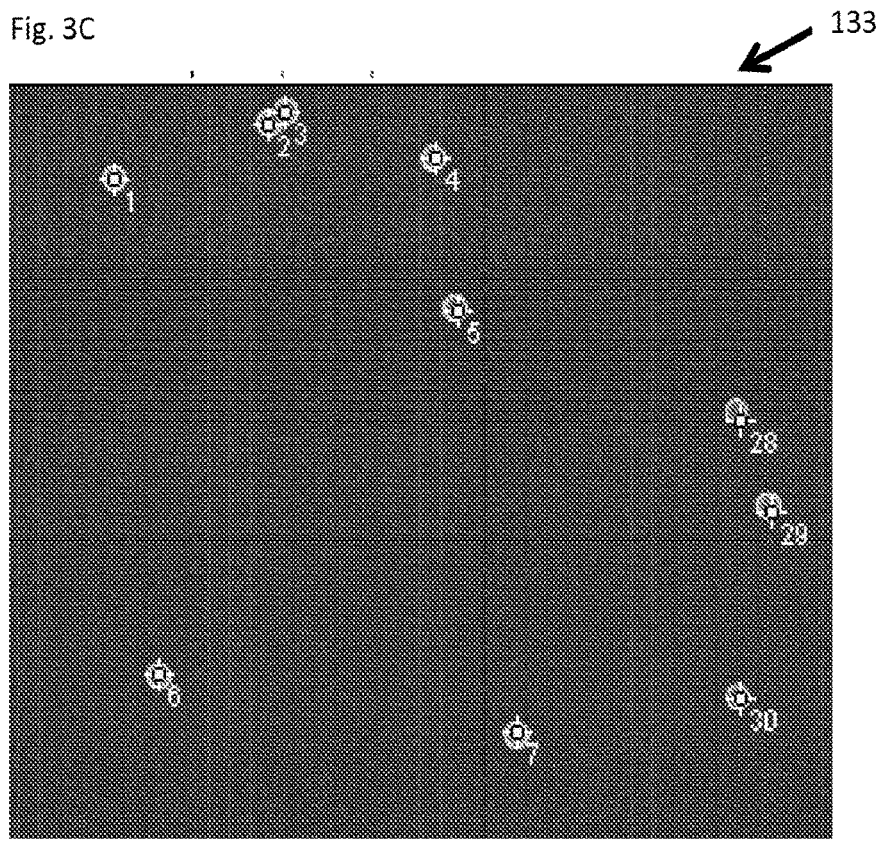
FIG. 3C is a close-up view of the SEM image of FIG. 3B above.

FIGS. 3A-3C are high magnification SEM images of polystyrene beads adhered to a poly-ether sulfone filter. FIG. 3A is an unprocessed image 130 and FIG. 3B is a detected and enumerated image 132. FIG. 3C is a close-up view 133 of the view of FIG. 3B and section 131 of FIG. 3A. In these example images, 77 particles were detected in a field of view of 131.47 $\mu m^2$. This corresponds to approximately 0.59 particles per $\mu m^2$. View 133 shows the numbered particles 1, 2, 3, 4, 5, 6, 7, 28, 29, 30.

Figure 4A:
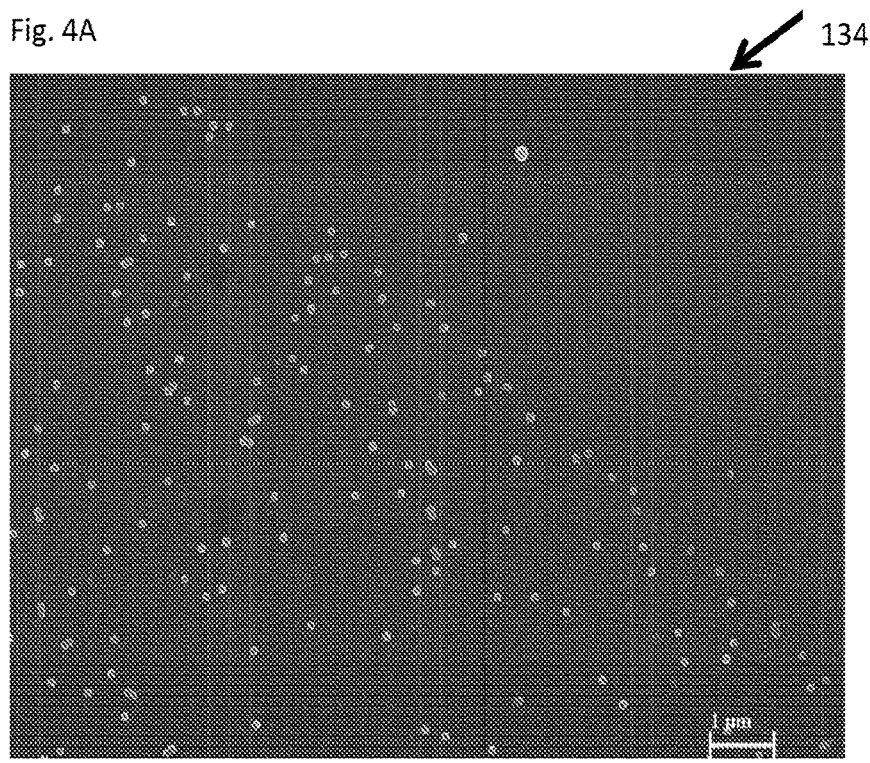
FIG. 4A is a schematic view of an edge of the droplet footprint image using SEM (primary electrons) at high magnification.
Figure 4B:
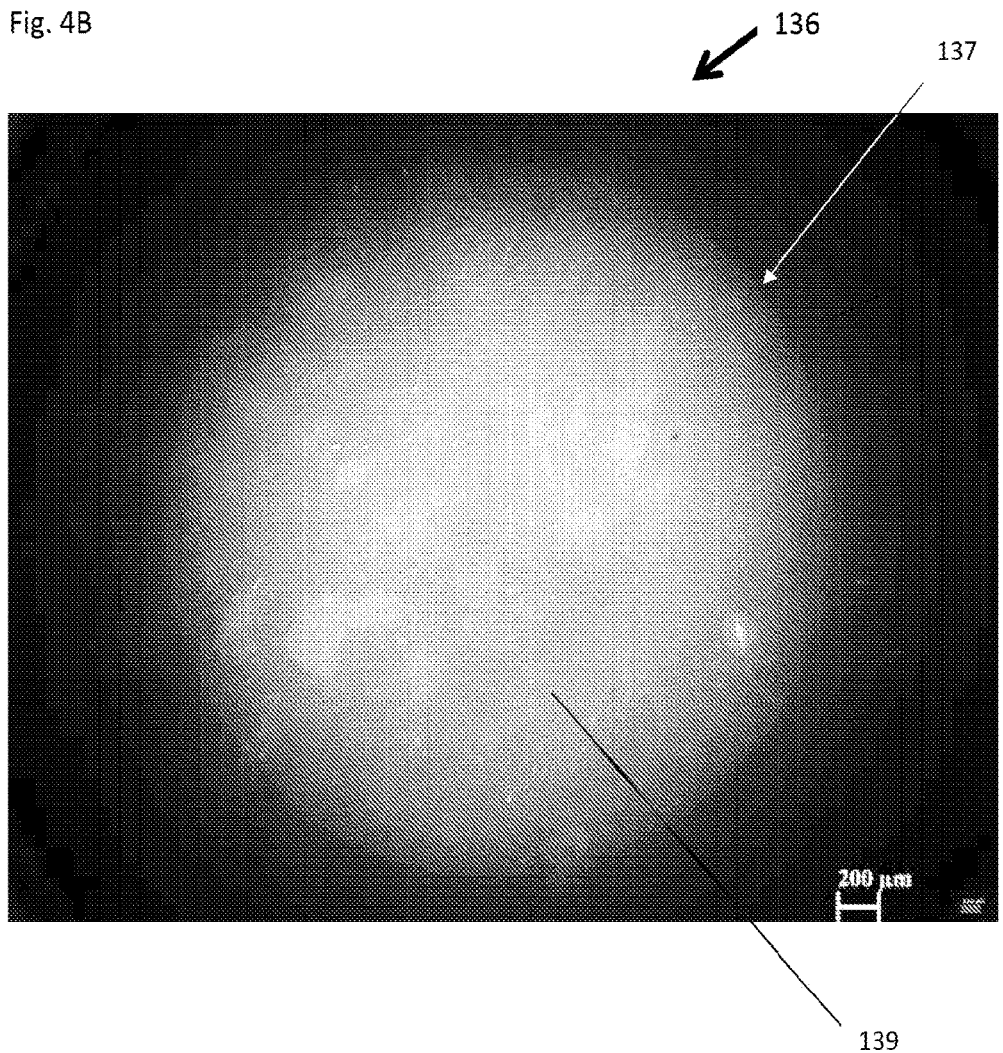
FIG. 4B is schematic view of an edge of the droplet footprint image using SEM (primary electrons) at low magnification.

FIGS. 4A-4B show the edge of the droplet footprint imaged using SEM (primary electrons). FIG. 4A show an image 134 at high magnification and FIG. 4B shows a footprint image 136 at low magnification. The location of the high magnification image 134, shown in FIG. 4A, is marked with a white arrow in FIG. 4B so that image 134 shows a portion of the entire footprint image 136. The edge of the droplet is well-defined with a negligible number of particles outside the footprint. At low magnification, the entire footprint 136 of the droplet is visualized and the area of the footprint can be precisely measured. In this example, the area of the footprint ($A_{total}$) was measured to 8.436 $mm^2$.

Figure 5A:
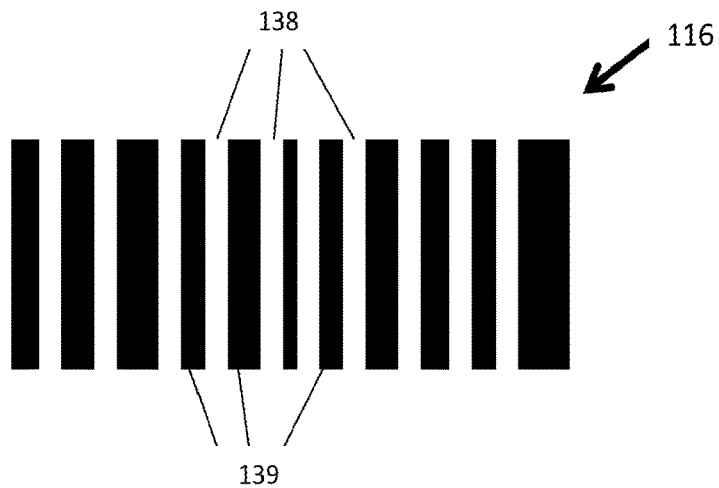
FIG. 5A is a cross-sectional schematic side view of the membrane of the present invention with open pores.
Figure 5B:
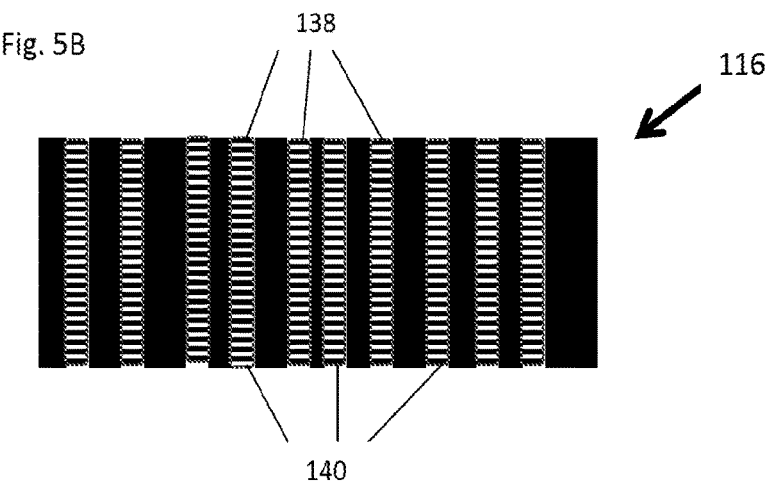
FIG. 5B is a cross-sectional schematic side view of the membrane shown in FIG. 5A but with sealed pores.
Figure 5C:
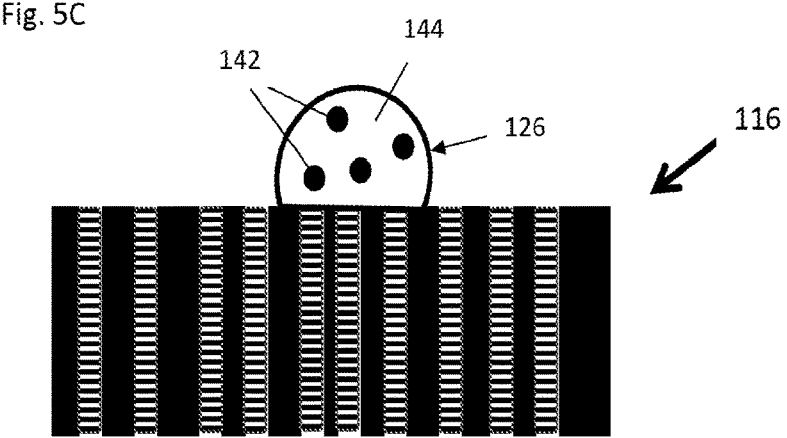
FIG. 5C is a cross-sectional schematic side view of the membrane of the present invention shown in FIG. 5B having a sample droplet deposited thereon.

FIGS. 5A-5D are cross-sectional side views of the filter membrane 116 and describe the process of sealing the filter membrane 116 and then dissolving the sealant. In FIG. 5A, the filter membrane 116 has open pores 138, defined between elongate grid members 139 of the filter membrane 116, that extends through the filter membrane 116. In FIG. 5B, the pores 138 are filled with a sealant 140. In FIG. 5C, the sample droplet 126 of sample 124, that is a liquid 144 containing particles 142 to be analyzed, is deposited onto the filter membrane 116. Preferably, the droplet 126 is deposited onto the filter membrane 116 by using the injector 118 described above. Upon contact by droplet 126 with sealant 140, liquid 144 dissolves sealant 140 that is disposed immediately below droplet 126 so that the liquid 144 is absorbed and passed through the pores 138 only disposed below droplet 126. Because particles to be enumarated 142 have a size that is greater than pores 138 of the membrane, the particles 142 are deposited on top the filter membrane 116 while the liquid and any smaller contaminants 144 are absorbed or flows into the pores 138 below the droplet 126 as the sealant 140 in those pores are dissolved and the liquid 144 is subject to the suction from elongate chamber 128 of vacuum chamber 104 below filter membrane 116.

Figure 5D:
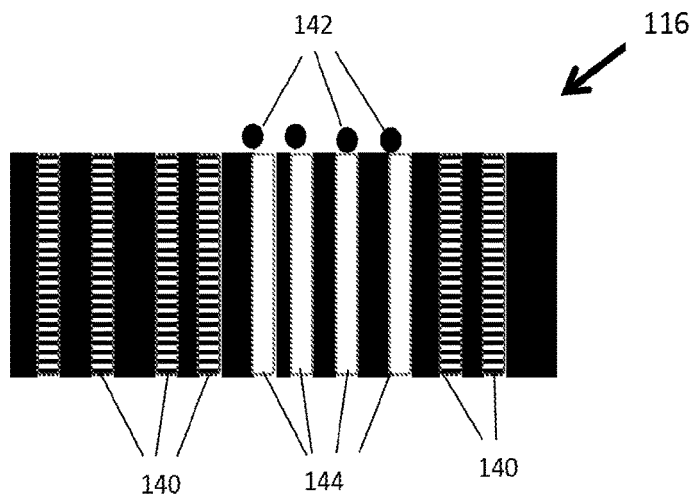
FIG. 5D is a cross-sectional schematic side view of the membrane shown in FIG. 5C having the droplet being absorbed into the membrane of the present invention.
Figure 6:
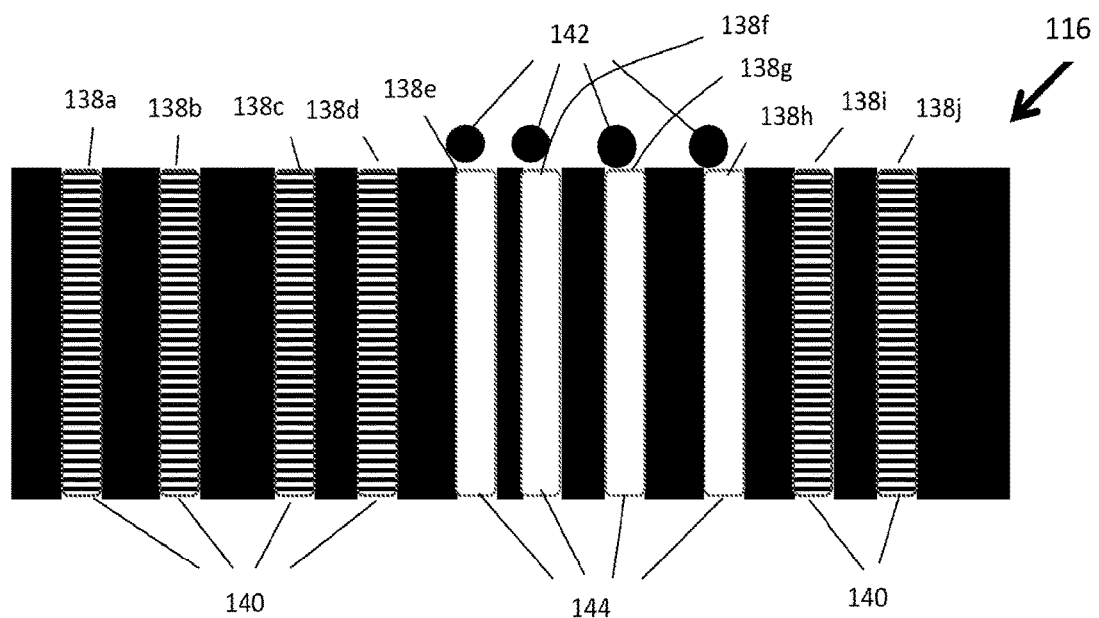
FIG. 6 is an enlarged view of FIG. 5D.

FIG. 6 is an enlarged view of the filter membrane 116 of FIG. 5D. The sub-visible particles 142 rest on the filter membrane 116 and the particles 142 are larger than the pores 138a-138j so they do not pass through the pores even if the pores are open and subject to suction from the vacuum chamber 104 (shown in FIG. 1). Pores 138a-d and 138i-j are still filled with sealant 140 since they have not been dissolved by the liquid 144 because they have not been in contact with the liquid 144 of sample droplet 126 (see FIG. 5C). More particularly, the diluent, such as a suitable buffer, in liquid 144 dissolves sealant 140. As indicated above, the diluent should be compatible with the specimen i.e. have minimal influence of the specimen morphology and aggregation state. The diluent should also have the property of dissolving the sealant. This is to make sure that the vacuum is only maintained at the footprint and so that the setup does not lose vacuum by "opening up" pores outside the area of interest. As the liquid 144 dissolves the sealant 140 disposed in pores 138e-138h, the liquid 144 fills pores 138e-138h to replace the sealant 140. This makes it easier to enumerate particles 142 because particles 142 are laying on top of filter segment 116 and are well-distributed across the filter membrane 116.

EXAMPLE

Below is an illustrative example of method of preparing the filter membrane 116 according to the present invention.

1. A sample, containing sub-visible particles 142, such as micro-particles and/or nanoparticles, is prepared for enumeration by diluting the sample in series in an appropriate diluent (typically water, phosphate-buffered, HEPES-buffered, TRIS-buffered or Histidine-buffered saline) depending on the buffer conditions of each particular sample.

2. A fixation agent (typically glutaraldehyde or formaldehyde) and/or a stabilizing agent (typically sucrose or glycerol) can be introduced into the diluted sample solution 124, that also includes the sub-visible particles 142, to stabilize and preserve the structure of the particles and in some samples prevent undesirable aggregation of the particles 142. The fixation/stabilizing agents and the diluent correspond to liquid 144 and together with the particles 142 form the sample/specimen 124 and sample droplet 126. The fixation/stabilizing agents are used to prevent the particles 142 from being destroyed or damaged during handling and from undesirably adhering to one another which make it more difficult to later enumerate the particles 142.

3. The filter assembly 112 consists of the porous filter membrane 116 (typically made of poly-ether sulfone or polycarbonate) with pores 138 that have a defined pore size (typically 0 to 15 nm) and an operable filter cassette made of plastic or equivalent are used for separating the particles 142 from the liquid. A suitable filter assembly 112 is best shown in FIG. 2. In general, the filters are bought in bulk as single-use filters and thus need to be mounted on something. Some vendors also sell filter holders and these devices are originally made to be connected to a syringe and push the liquid through and thus not sucking the liquid through using vacuum. It is therefore necessary to mount the filter to a filter assembly to assure vacuum integrity. After some experimentation it was surprisingly realized that the filter could be mounted directly on the SEM support which saves time and avoids the critical steps of manually handling the specimen containing filters. It is conceivable that such an assembly can be inexpensively made and be sold as a SEM consumable.

4. The filter assembly 112 is mounted onto the top of the plastic vacuum chamber 104 which in turn is connected to the vacuum device 102 via tubing 106.

5. The vacuum in the vacuum chamber 104 is controlled by the 3-way Luer valve 108 and monitored by using the vacuum manometer 110. An automatic system using magnetic valves controlled by an electronic monitoring system can also be implemented.

6. The pores 138 in the filter membrane 116 are preferably sealed with sealant 140 such as glycine (or equivalent) prior to sample application of the sample droplet 126, as best shown in FIGS. 5B and 5C. It was surprisingly and unexpectedly discovered that by using sealant 140 in the filter membrane 116, the particles 142 inside droplet 126 were distributed more evenly (prior to removing the liquid 144 of the droplet 126) and there was no need to use a high vacuum force to reduce the risk of the droplet spreading out unevenly on the filter membrane. It should be noted that the distribution of the particles does not have to be the same at the outer periphery and as it is at the center. The pattern of the particle distribution can be determined by scanning the footprint 134/136 (see FIGS. 4A-4B) of the particle sample, disposed on the filter membrane, from the outer periphery or outer edge 137 of the foot print 136 towards the center 139 of the footprint of the particle sample. If the scanned portion of the particle sample shows a certain pattern of distribution of particles, it can be reliably assumed that the same particle distribution pattern apply around the entire circular-shaped particle sample footprint 136 partly because the particles were given time to settle before the sealant 140 is dissolved by the liquid in the droplet 126. Because the droplet 126 is first deposited onto the sealed filter membrane 116 the outer edge 137 of footprint 136 of the droplet 126 becomes relatively distinct or sharp which is important in order to determine where to start the enumeration and scanning towards the center 139 of the circular-shaped particle sample or footprint 136 deposited on the dissolved filter membrane 116. It was unexpectedly discovered that the advantages of the relatively even distribution of the particles on the filter membrane outweighed the drawbacks of having to remove the sealant to permit the liquid in the droplet to flow through the filter membrane before starting the enumeration of the particles. Any uneven or non-distinct periphery of the footprint of the droplet on the filter membrane makes it more difficult to determine the footprint thereof and know which area is to be analyzed in order to count all the particles in the droplet. By applying the sample droplet 126 onto the filter membrane 116, with all the pores 138 being sealed by sealant 140, the particles 142 are evenly distributed inside droplet 126 as the droplet 126 spreads out on the sealed top surface of filter membrane 116. The requirement of having to dissolve the sealant 140 first slows down the flow-through of the liquid 144 through the pores 138. By not using the sealant 140, the liquid 144 of the droplet 126 would immediately start to flow through the pores 138 and because the droplet 126 is thickest at the center and thinner at its periphery more particles 142 tend to be located in the middle of the droplet. This often results in an uneven distribution of the particles onto the filter membrane and the outer edge of the foot print of the particles sample is not clear. It should be noted more particles are not always located in the middle of the droplet because some specimen may have a tendency to concentrate towards the air-water interface. It is generally difficult to exactly foresee how different samples behave and distribute.

Since the entire footprint 136 of the sample droplet 126 is used to calculate the particle concentration of particles 142, the droplet 126 should not touch the inner edge of the filter holder of filter membrane 116. Thus, it is important that only a defined part of the filter membrane 116 is covered with the sample droplet 126. This is to make sure that all the particles 142 in the droplet 126 are enumerated or counted. Also, the position of sample droplet 126 should be aligned with cavity 129 and channel 128 defined inside stub 120. Without pretreatment of the filter membrane 116 with sealant 140, the surrounding filter pores, i.e. pores 138$a$-138$d$ and 138$i$-138$j$ in FIG. 6, remain open and air flows around the droplet 126 and through the filter membrane 116 so that the sample droplet 126 does not absorb and becomes filtered fast enough to get a good sample distribution of the particles 142. In other words, the use of the sealant 140 has the advantage of creating a more distinct outer periphery 137 of the footprint 136 of droplet 126 when liquid starts to dissolve sealant 140 that is deposed below droplet 126. Without the use of sealant 140 there is not enough time for the particles 142 to be evenly distributed inside droplet 126 since the liquid 144 immediately starts to flow through the pores 138 without giving the particles 142 time to settle and be evenly distributed inside droplet 126. One very important feature of sealant 140 is thus to create a vacuum condition so that a defined specimen footprint is formed. More particularly, without the treatment of the sealant 140 according to the present invention, the droplet 126 undesirably dries through diffusion and evaporation. This results in a highly uneven particle distribution due to the drying effects. It was surprisingly discovered that the undesirable evaporation may cause osmotic effects potentially causing particle disruption and crystal formation due to increased salt concentration in the remaining droplet. Additionally, this obscures the particle detection and enumeration caused by broken particles and particles that are hidden by salt precipitates. In the present invention, when applying the sample droplet 126 onto the sealed filter membrane 116, the liquid 144 in the sample droplet 126 slowly dissolves the sealant 140 to open the pores 138$e$-138$h$ disposed underneath the droplet 126. Consequently, the liquid 144 is rapidly drawn through the pores 138$e$-138$h$ of filter membrane 116 by the vacuum, resulting in a good sample distribution of particles 142 on the top surface of filter membrane 116.

7. Before applying the sample droplet 126 onto the filter membrane 116, the vacuum device 102 is activated and the pressure in the vacuum chamber 104 is lowered to create suction on the filter membrane 116. The vacuum in the vacuum chamber 104 ensures that the liquid 144 of droplet 126 is absorbed evenly on the filter membrane 116. The combination of the usage of the sealant and the vacuum results in an even distribution of particles 142 across the footprint 136 on the filter membrane 116.

8. A suitable volume (typically 5 µl) of the sample droplet 126 is applied on the porous and sealed filter membrane 116. As indicated above, it is important that the diameters of the particles 142 are greater than the diameter of pores 138 of filter membrane 116 and that the droplet 126 does not touch the edges of the filter mount. A higher volume than 5 µl can be applied by using an injection system where either multiple drops or larger volumes are applied on the same position on the filter membrane 116. In general, the use of larger volumes minimizes the sampling error and allows the analysis of less concentrated samples.

9. The sample droplet 126 is absorbed on the filter membrane 116 for typically 60 seconds under vacuum pressure provided by vacuum chamber 104. The exact pressure values may have to be adjusted partly depending on pore size, sample type, volume, purity and viscosity.

10. After absorption, the filter membrane 116 may be detached from the filter assembly 112 mounted onto the SEM alumina stub 120 (typically by using an adhesive and conductive carbon tape 122).

11. The filter membrane 116, with bound particles 142 placed thereon, may then be sputter coated by for example a thin film of carbon (typically 20 nm thick) using a carbon evaporator at a suitable chamber pressure typically $1 \times 10^{-5}$ mbar. The sputter coating improves the conductivity of the filter membrane 116; increases the signal to noise ratio of the filter membrane 116 and reduces the electron beam damage and charging effects. This technique is often necessary to use in order to image a filter material using a SEM. It may be unconventional to use carbon coating but it provides higher resolution SEM imaging compared to the larger grain size of metal sputtering.

12. The filter membrane 116 may be transferred to the SEM and the signal from scattered primary electrons (using an in-lens detector) or secondary electrons (such as by using a SE2 detector) is recorded both at low to cover the entire footprint and high magnification (typically 10 000 to 30 000) for enumeration. If a reference standard with a different secondary electron signature is used (albeit not necessary to determine the particle concentration) the particles of interest can be distinguished from the reference particles by combining intensity information from different detectors (such as in-lens and SE2 detectors).

13. The low magnification images 136 (see FIG. 4B) are used to define the size of the footprint of the droplet and the overall specimen distribution while the high magnification images are used to determine the particle enumeration.

14. The high magnification images, such as image 134, are acquired across the sample footprint starting from the edge 137, through the center 139 and to the opposite edge of the droplet in order to minimize any effect of differences in particle distribution across the footprint of the droplet.

15. From the low magnification images, such as image 136, the area of the sample footprint ($A_{total}$) is calculated by tracing the edge of the footprint. The encircled pixels are counted and the number counted is multiplied with the pixel size.

16. From the high magnification images, the particles 142 are detected and counted. This procedure can be performed through manual marking or automated marking by using suitable software such as Vironova's proprietary software Analyzer or any other appropriate image analysis software. The average number of particles per area unit ($n/A_{FOV}$) is calculated from the image dataset.

17. The number of particles per mL in the particle sample is, preferably, calculated by using the following formula:

$$C = A_{total} \times \frac{n}{A_{FOV}} \times df \times \frac{1000 \text{ µl}}{V \text{ µl}}$$

Where C is the concentration of particles, df is the dilution factor and V is the applied volume of sample. It may also be possible to use a formula that takes into account that the particle distribution may vary from the periphery of the particle sample as the sample is scanned towards the center thereof.

In summary, the particle quantitative scanning electron microscopy (pqSEM) technique of the present invention is a high-precision direct particle detection and enumeration technique. An important feature of the present invention is that the direct detection does not depend on the affinity between a probe and the specimen which many existing conventional techniques do. All parameters, such as the dilution factor, the applied volume, the footprint of the droplet can be controlled and the number of particles per area unit can be directly measured while minimizing the error from approximations and assumptions. Moreover, the resolving power of the pqSEM permits detection of individual sub-visible particles within clusters and two populations of particles of different sizes or other morphological features can be enumerated from the same sample. The particles and the footprint from the high-contrast images generated by the pqSEM technique of the present invention can readily be detected by using automated image analysis. This provides the means for rapidly collecting large datasets and producing robust statistical results.

While the present invention has been described in accordance with preferred compositions and embodiments, it is to be understood that certain substitutions and alterations may be made thereto without departing from the spirit and scope of the following claims.

We claim:

1. A method for quantification of sub-visible particles, comprising: providing a filter membrane having a plurality of pores defined therethrough, the filter membrane being in operational engagement with a vacuum chamber; sealing the pores with a sealant; applying a sample droplet, containing a liquid and sub-visible particles, onto the filter membrane without the sample droplet touching any outside edge of the filter membrane; the liquid dissolving the sealant in pores disposed below the sample droplet; the liquid flowing through the pores in which the sealant has been dissolved and the sub-visible particles remaining on top of the filter membrane; and the sub-visible particles being enumerated in an electron microscopy;

wherein the method further comprises the step of pre-mounting a filter assembly containing the filter membrane, onto a SEM support.

2. The method of claim 1 wherein the method further comprises the step of placing a mounting tape on the SEM support.

3. The method of claim 1 wherein the method further comprises the step of providing the SEM support having an elongate channel defined therein, using an injector containing the sample droplet, and aligning the injector on top of an elongate channel prior to depositing the sample droplet on the filter membrane.

4. The method of claim 1 wherein the method further comprises the step of connecting the SEM support to a vacuum chamber connected to a vacuum source and subjecting the filter membrane to a suction force via the elongate channel.

5. The method of claim 1 wherein the method further comprises the step of the liquid only dissolving the sealant in the pores disposed immediately below sample droplet while adjacent pores remain sealed with the sealant.

6. The method of claim 1 wherein the method further comprises the step of the sub-visible particles forming a footprint on the filter membrane and scanning the sub-particles from an outside periphery of the footprint towards a center of the footprint.

7. The method of claim 1 wherein the method further comprises the step of using a diluent of the liquid to dissolve the sealant in the pores located directly below the sample droplet.

8. The method of claim 1 wherein the method further comprises the step of using glycine as the sealant.

* * * * *